(12) United States Patent
Davenport et al.

(10) Patent No.: US 10,806,598 B2
(45) Date of Patent: Oct. 20, 2020

(54) IMPLANT INSERTER

(71) Applicant: GLOBUS MEDICAL, INC., Audubon, PA (US)

(72) Inventors: Daniel Davenport, Collegeville, PA (US); Mark Adams, Downingtown, PA (US); Michael Zweizig, Fleetwood, PA (US)

(73) Assignee: Globus Medical, Inc., Audubon, PA (US)

(*) Notice: Subject to any disclaimer, the term of this patent is extended or adjusted under 35 U.S.C. 154(b) by 108 days.

(21) Appl. No.: 15/906,133

(22) Filed: Feb. 27, 2018

(65) Prior Publication Data

US 2018/0185170 A1 Jul. 5, 2018

Related U.S. Application Data

(63) Continuation of application No. 14/878,027, filed on Oct. 8, 2015, now Pat. No. 9,937,061, which is a continuation of application No. 13/408,188, filed on Feb. 29, 2012, now Pat. No. 9,186,263.

(51) Int. Cl.
A61F 2/46 (2006.01)
A61F 2/44 (2006.01)
A61B 17/02 (2006.01)
A61F 2/30 (2006.01)

(52) U.S. Cl.
CPC .......... A61F 2/4611 (2013.01); A61F 2/4465 (2013.01); A61B 2017/0256 (2013.01); A61F 2002/30593 (2013.01); A61F 2002/30774 (2013.01); A61F 2002/30782 (2013.01); A61F 2002/30787 (2013.01); A61F 2002/30828 (2013.01); A61F 2002/30843 (2013.01); A61F 2002/4627 (2013.01); A61F 2002/4628 (2013.01); A61F 2002/4629 (2013.01)

(58) Field of Classification Search
CPC ..... A61B 2017/0256; A61F 2002/4629; A61F 2002/4628; A61F 2002/4627; A61F 2/4611

See application file for complete search history.

(56) References Cited

U.S. PATENT DOCUMENTS

| 5,431,658 | A | 7/1995 | Moskovich |
| 7,625,379 | B2 | 12/2009 | Puno |
| 7,722,622 | B2 | 5/2010 | Evans |
| 7,766,918 | B2 | 8/2010 | Allard et al. |
| 8,062,303 | B2 | 11/2011 | Berry et al. |

(Continued)

Primary Examiner — Ellen C Hammond

(57) ABSTRACT

An apparatus for inserting an implant between vertebrae includes a body having a through bore, a central shaft movable within the through bore, the central shaft having a proximal end and a distal end. The apparatus includes a pair of distractor arms having proximal portions and distal portions, the proximal portions pivotally coupled to the body and distal portions for engagement between the vertebrae. Tracking slots are formed in and extend through surfaces of and along a longitudinal axes of the distractor arms and an attachment tip is operably connected to the central shaft, the attachment tip is configured to grip the implant. The apparatus includes a single guide member projecting outward from the attachment tip and the attachment tip is removably connectable to the central shaft in multiple configurations.

20 Claims, 5 Drawing Sheets

(56) References Cited

U.S. PATENT DOCUMENTS

| | | |
|---|---|---|
| 8,377,072 B2 | 2/2013 | Stad et al. |
| 8,540,721 B2 | 9/2013 | Lee et al. |
| 2002/0116009 A1 | 8/2002 | Fraser et al. |
| 2004/0225295 A1 | 11/2004 | Zubok et al. |
| 2005/0165408 A1 | 7/2005 | Puno et al. |
| 2007/0123903 A1 | 5/2007 | Raymond |
| 2007/0185375 A1 | 8/2007 | Stad |
| 2008/0177275 A1 | 7/2008 | Wing et al. |
| 2008/0241641 A1 | 10/2008 | Kurita et al. |
| 2008/0269764 A1 | 10/2008 | Blain |
| 2009/0005784 A1 | 1/2009 | Blain |
| 2009/0030422 A1 | 1/2009 | Parsons et al. |
| 2009/0048604 A1 | 2/2009 | Milz |
| 2009/0209967 A1 | 8/2009 | Evans |
| 2010/0069914 A1 | 3/2010 | Puno |
| 2010/0160963 A1 | 6/2010 | Runco |
| 2010/0262154 A1 | 10/2010 | Evans |
| 2012/0059477 A1* | 3/2012 | Kleiner .................. A61F 2/442 623/17.16 |

* cited by examiner

IMPLANT INSERTER

CROSS-REFERENCE TO RELATED APPLICATIONS

This patent application is a continuation of U.S. patent application Ser. No. 14/878,027 filed on Oct. 8, 2015 (published as U.S. Patent Publication No. 2016/0022439), which is a continuation of U.S. patent application Ser. No. 13/408, 188 filed on Feb. 29, 2012 (now issued as U.S. Pat. No. 9,186,263), the entire disclosures of which are incorporated herein by reference in their entireties for all purposes.

FIELD OF THE INVENTION

The present disclosure relates generally to devices used to install implants between vertebrae.

BACKGROUND OF THE INVENTION

Portions of the spine are linked together in part by intervertebral discs, which are discs that lie between vertebrae. Damage to these discs can result from sports injuries, accidents, infections, wear and tear over time and other causes. One type of treatment for this damage, involves removal of the damaged disc between vertebrae and insertion of an implant into the disc space. The insertion of the implant can maintain the natural separation between vertebrae.

Spinal inserter instruments can be used to install implants between vertebrae. These devices are usually operated manually and can include elements such as distractor arms to spread apart the disc space and a shaft with a holder used to grip the implant and move it into position. After the implant is inserted, the instrument can be removed.

SUMMARY OF THE INVENTION

An apparatus for inserting an implant between vertebrae includes a body having a through bore, a central shaft movable within the through bore, the central shaft having a proximal end and a distal end. The apparatus includes a pair of distractor arms having proximal portions and distal portions, the proximal portions pivotally coupled to the body and distal portions for engagement between the vertebrae. Tracking slots are formed in and extend through surfaces of and along a longitudinal axes of the distractor arms and an attachment tip is operably connected to the central shaft, the attachment tip is configured to grip the implant. The apparatus includes a single guide member projecting outward from the attachment tip and the attachment tip is removably connectable to the central shaft in multiple configurations.

BRIEF DESCRIPTION OF THE DRAWINGS

The various embodiments disclosed herein are illustrated by way of example and not by way of limitation in the figures of the accompanying drawings, in which like reference numerals refer to similar elements.

DETAILED DESCRIPTION OF THE INVENTION

Figure 1:
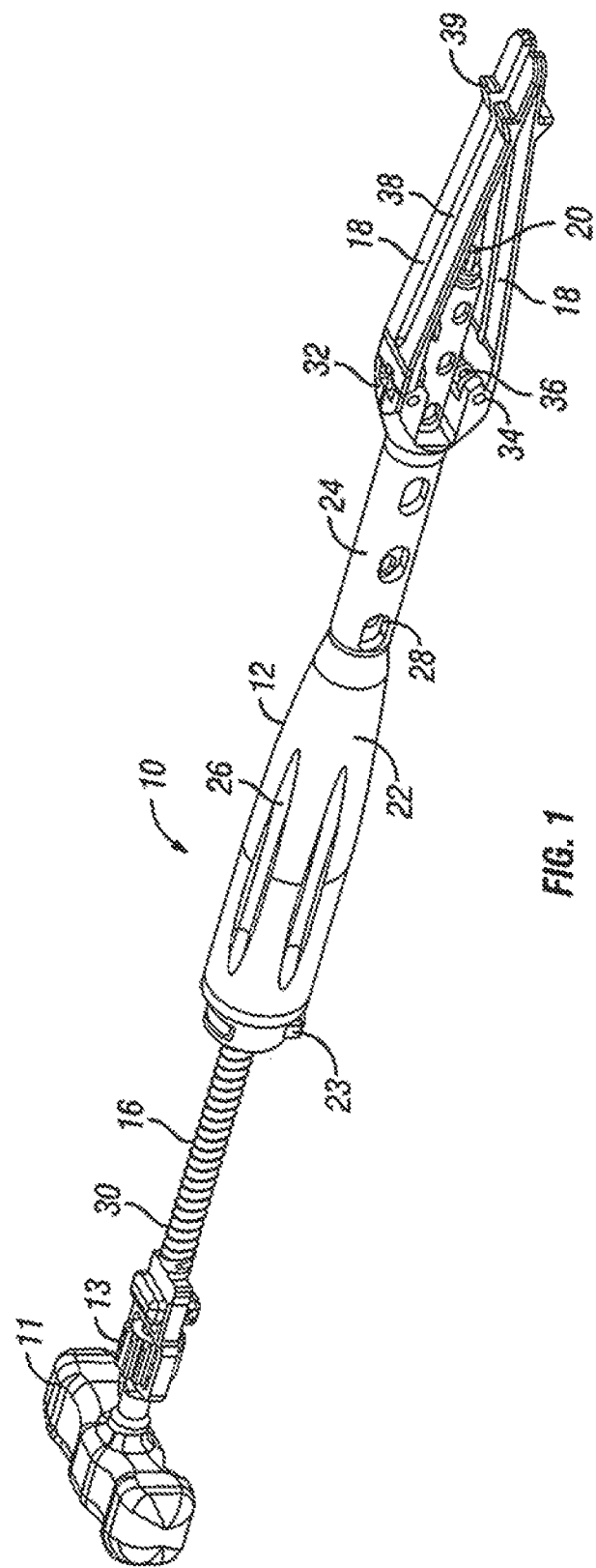
FIG. 1 is a perspective view of an example embodiment of an implant inserter.
Figure 2:
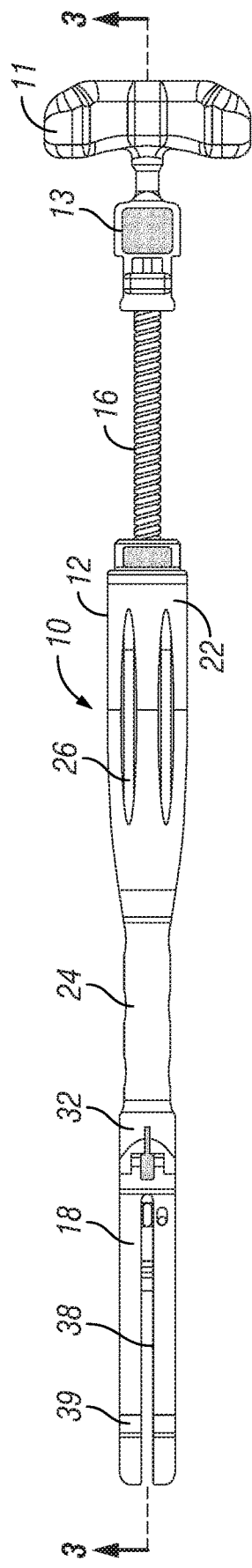
FIG. 2 is a top view of the implant inserter shown in FIG. 1.
Figure 3:
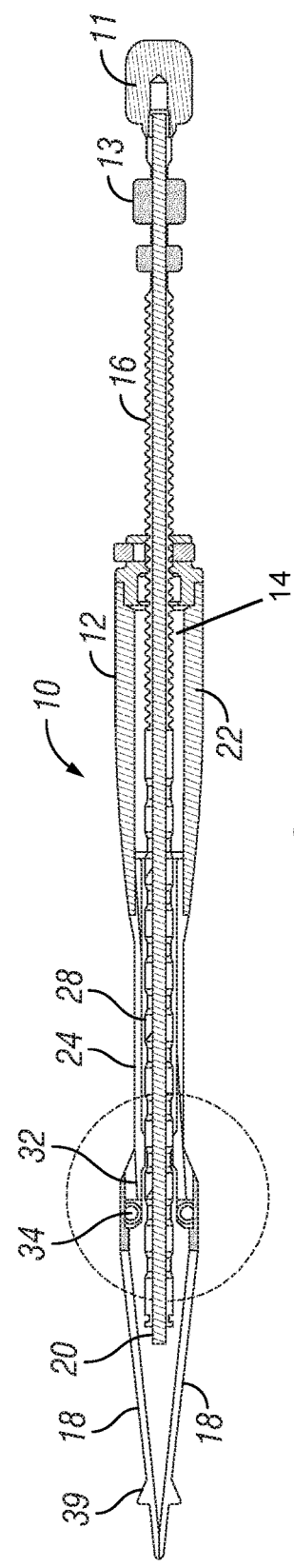
FIG. 3 is a sectional view taken on line A-A of FIG. 2.

FIGS. 1-3, illustrate an embodiment of an implant inserter 10 for inserting an implant between vertebrae (not shown). The implant inserter 10 can include a body 12 that has a bore 14 and a central shaft 16 that is movable through the bore 14. The central shaft 16 has a proximal end (closer to the user) and a distal end (closer to the surgical site). A pair of distractor arms 18 have proximal portions pivotally coupled to the body 12 and distal portions for engagement between the vertebrae. The central shaft 16 includes a tip adapter 20 located at its distal end.

Figure 5:
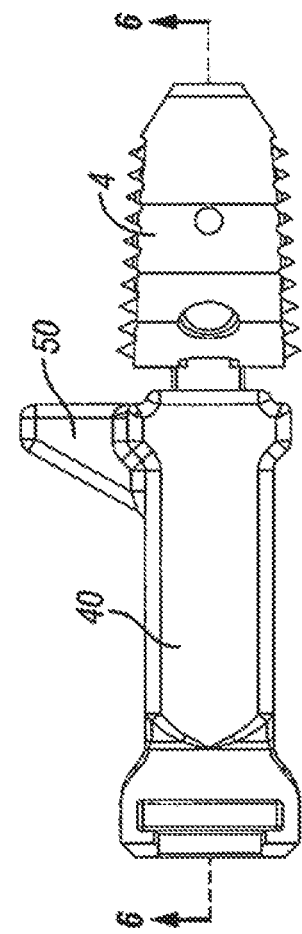
FIG. 5 is a side view of the attachment tip shown in FIG. 4.
Figure 7:
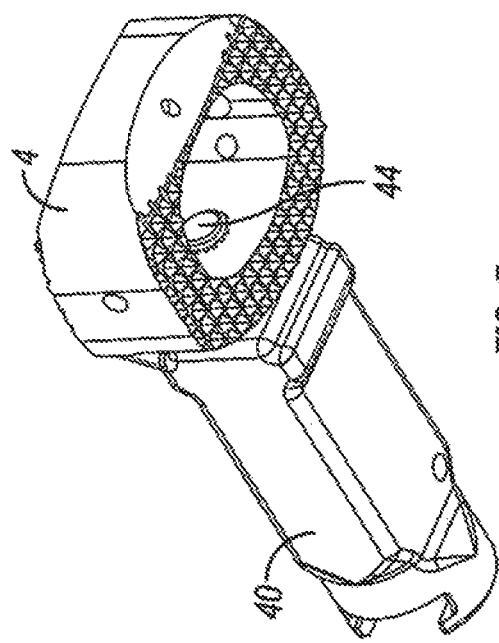
FIG. 7 is a perspective view of the attachment tip of FIG. 4 with the example implant of FIG. 6.
Figure 4:
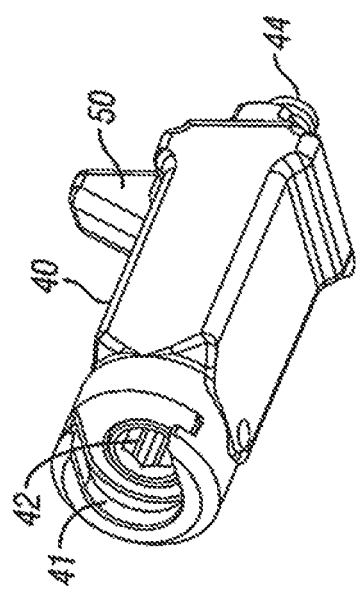
FIG. 4 is a perspective view of an example embodiment of an attachment tip that can be used with the implant inserter of FIG. 1.
Figure 6:
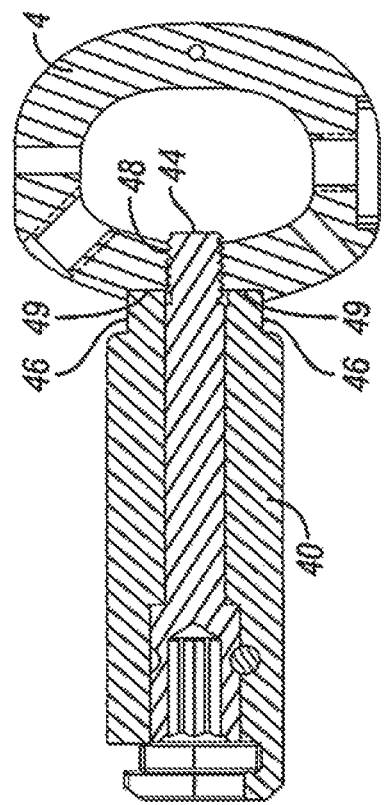
FIG. 6 is a top sectional view taken on line A-A of FIG. 5 with an example embodiment of an implant.

Referring to FIGS. 1, 4, and 5, in one embodiment, an attachment tip 40 is operably connected to the tip adapter 20 and central shaft 16. The attachment tip 40 is configured to grip the implant 4 in a manner that the implant 4 can be easily inserted between the vertebrae. Referring to FIGS. 1, 3, and 4, the attachment tip 40 is designed to be attached in multiple configurations relative to the general plane of operation of the implant inserter 10. The attachment tip in part ensures proper guidance, alignment and insertion of the implant.

Referring to FIGS. 1-3, in an embodiment, the body 12 includes a first tubular portion 22 and a second tubular portion 24. The first tubular portion 22 may be centrally located so that a user can optionally hold it for support and guidance during operation of the implant inserter 10. The first tubular portion 22 includes recesses 26 formed therein to provide texture for the user's grip. In an example embodiment, the first tubular portion 22 has internal threads (not shown) formed at its distal end and configured to accept external threads that can be formed on the central shaft 16. The shaft includes a handle 11 for ease of use and operation.

The first tubular portion 22 has a clutch mechanism or actuator 23, that can have an off position and an engaged position. In an example embodiment, when the actuator 23 is in the off position, the central shaft slides freely and can be driven longitudinally straight forward in a distal direction. In an alternative approach the actuator 23 can be moved to the engaged position. When the actuator 23 is in the engaged position, the central shaft 16 does not slide freely, however it can be moved forward through rotation of the handle.

When the central shaft 16 is moved forward in the engaged position with rotational drive action, the external threads and internal threads will engage. In an embodiment, the actuator 23 is a push button. It can also be a cam mechanism. Any suitable clutch mechanism can be used for the actuator 23. In an alternative embodiment, the actuator 23 may include a mode that allows for the user to use a ratchet type action to drive the central shaft 16 forward. In an embodiment, a dial 13 positioned just distal to the handle 11 and can be rotated to move the tip adapter to engage and disengage the implant. The dial 13 provides precision control.

Referring again to FIGS. 1-3, in one embodiment, the body can have a second tubular portion 24 that is tapered and extends from a distal end of the body 12. The second tubular 24 portion provides an additional guiding support for the central shaft 16. Windows 28 are included in the second tubular portion 24 so that a user can track the progress of the central shaft 16.

In an embodiment, the first tubular portion 22 and second tubular portion 24 are generally circular in cross section. However, any cross sectional shape could be used, for example but not limited to rectangular, elliptical or square. The first tubular portion 22 and the second tubular portion 24 can be joined using an interference fit, adhesive or a threaded connection. Alternatively, the first tubular portion 22 and second tubular portion 24 can be monolithically molded as one piece. In an example embodiment, the first tubular portion and second tubular portion may be comprised of aluminum, steel, plastic, and/or silicone. However, any material suitable for surgical applications may be used, such as but not limited to plastic, composite and metal.

Referring to FIGS. 1-3 the central shaft 16 has a proximal end and a distal end. In an example embodiment, the proximal end of the central shaft includes external threads 30 sized and configured to join with internal threads formed on the first tubular portion 22 of the body 12. The remaining distal portion of the central shaft 16 can be straight without threads or can include ball, triangular, trapezoidal, and/or square screws. In an example embodiment, the central shaft 16 is circular in cross section. In alternate embodiments, the central shaft 16 can be any cross sectional shape such as but not limited to elliptical, square or rectangular. The central shaft may be made of steel. However, any material suitable for surgical applications may be used, such as but not limited to plastic, composite and metal.

In an embodiment, a tip adapter 20 is formed at the distal end of the central shaft 16. The tip adapter 20 and the distal end of the central shaft are sized and shaped to interface with and retain the attachment tip 40.

Referring to FIG. 1, in an example embodiment, a pair of distractor arms 18 are pivotally coupled to the second tubular portion 24 of the body 12. The distractor arms 18 are attachable to a coupling adapter 32 including two slots 34. The coupling adapter 32 is releasably attached to the second tubular portion 24. In another embodiment, the second tubular portion 24 and the coupling adapter 34 are formed as one monolithic piece.

Coupling pins 36 can be placed through slots 34 to join proximal ends of the distractor arms 18 to the coupling adapter 32. This configuration permits the distractor arms 18 to freely pivot. Also, distractor arms 18 can easily be interchanged for different sizes depending upon the particular requirements of the user, procedure, and surgical application. In addition to providing interchangeability, this configuration allows for distractor arms 18 to be easily removed for cleaning and sterilization.

In an example embodiment, at least one of the distractor arms 18 includes a tracking slot 38 extending along its length from the proximal to distal ends. Stop members 39 are formed at the distal ends of the distractor arms 18 and are shaped and configured to abut against vertebrae to provide stability during the operation of the inserter instrument. In an example embodiment, the stop members 39 include a forward rectangular endface designed to abut the vertebrae. In another embodiment, the stop members 39 can be adjustable for varying depths.

Referring to FIGS. 2-4, the attachment tip 40 can be operably connected to the central shaft 16. The proximal end of the attachment tip 40 includes a detent groove 41 and also has an internally disposed central bore 42. The detent groove 41 is designed to interface with a corresponding rib (not shown) on the central shaft 16. In one embodiment, the tip adapter 20 and central shaft 16 are attached by threading the tip adapter 20 into the central bore 42 and sliding the rib on the second tubular portion 24 into the detent groove 41 to provide a secure connection between the central shaft 16 and the attachment tip 40. As tip adapter 20 is slid, the attachment tip 40 slides onto the central shaft 16 through detent groove 41, causing the slider to capture the attachment tip 40.

Referring to FIGS. 4-7, a distal face of the attachment tip 40 includes fastening features configured to grip and retain an implant. In an example embodiment, the fastening features include a screw thread tip 44 and a rib 46. Referring to FIG. 5, implant 4 may include a tapped recess 48 that is sized and shaped to cooperate with threads on the screw thread tip 44. In an example embodiment, implant 4 can also include recesses 49 adapted to cooperate with ribs 46 to provide an interference fit between attachment tip 40 and implant 4.

Referring to FIGS. 1, 3, and 4-7, in an embodiment, a guide member or fin 50 projects in a generally orthogonal outward direction from the attachment tip 40. Fin 50 is sized, shaped and configured to slide within tracking slot 38 of guide member 18 to help guide the attachment tip 40 towards moving the implant 4 into a proper position between the vertebrae. The guide member or fin 50 may also be configured to slide on the outside of the guide member 18.

In one embodiment, the fin 50 is monolithically formed as part of the attachment tip 40. In other embodiments, the fin 50 is a separate piece that can be secured to the attachment tip 40 in a number of ways including but not limited to using a rib and recess, rail and groove, a fastener or adhesive. In an example embodiment, the fin 50 is triangular shaped in cross section or tapered. However, the fin 50 may have any size or shape suitable to cooperate with the tracking slot.

Referring to FIGS. 1 and 8-11, an example alternative embodiment of a pronged attachment tip 52 is shown. The pronged attachment tip 52 can be operably connected to the central shaft 16. The proximal end of the pronged attachment tip 52 includes a detent groove 51 and also has an internally disposed central bore 52. The detent groove 51 interfaces with a corresponding rib (not shown) on the central shaft 16.

A distal surface of the pronged attachment tip 52 has a base portion 54 with fastening features configured to releasably grip an implant 6. In an example embodiment, the fastening features include a pair of prongs 56 pivotally attached to the base portion 54. A support shaft 58 extends distally outward between the prongs 56. Prongs 56 have distal end faces 55 including inwardly facing ribs 57. In an embodiment, prongs 56 also include distal slots 53 and lateral openings 59.

Referring to FIGS. 8-11, in an embodiment, a support member 60 is attached to the distal portion of the pronged attachment tip 52. The support member has pins 62 designed to ride in the distal slots 53. A central recess 64 is disposed within the support member 60 and sized and shaped to receive the support shaft 58. In one embodiment, the support shaft 58 has threads and the central recess 64 may be tapped to correspond to the threads formed on the support shaft 58.

Referring to FIGS. 1 and 8-11, in one embodiment, guide member or fin 66 projects in a generally orthogonal outward direction from the pronged attachment tip 52. Fin 66 is sized, shaped and configured to slide within tracking slot 38 of guide member 18 to help guide the pronged attachment tip 52 and the implant 6 into a proper position between the vertebrae.

In one embodiment, the fin 66 may be monolithically formed as part of the pronged attachment tip 52. In other embodiments, the fin 66 is a separate piece that can be secured to the pronged attachment tip 52 in a number of ways including but not limited to using a rib and recess, rail and groove, a fastener or adhesive. In an example embodiment, the fin 66 is triangular shaped in cross section or tapered. However, the fin 66 may have any size or shape suitable to cooperate with the tracking slot 38.

Figure 8:
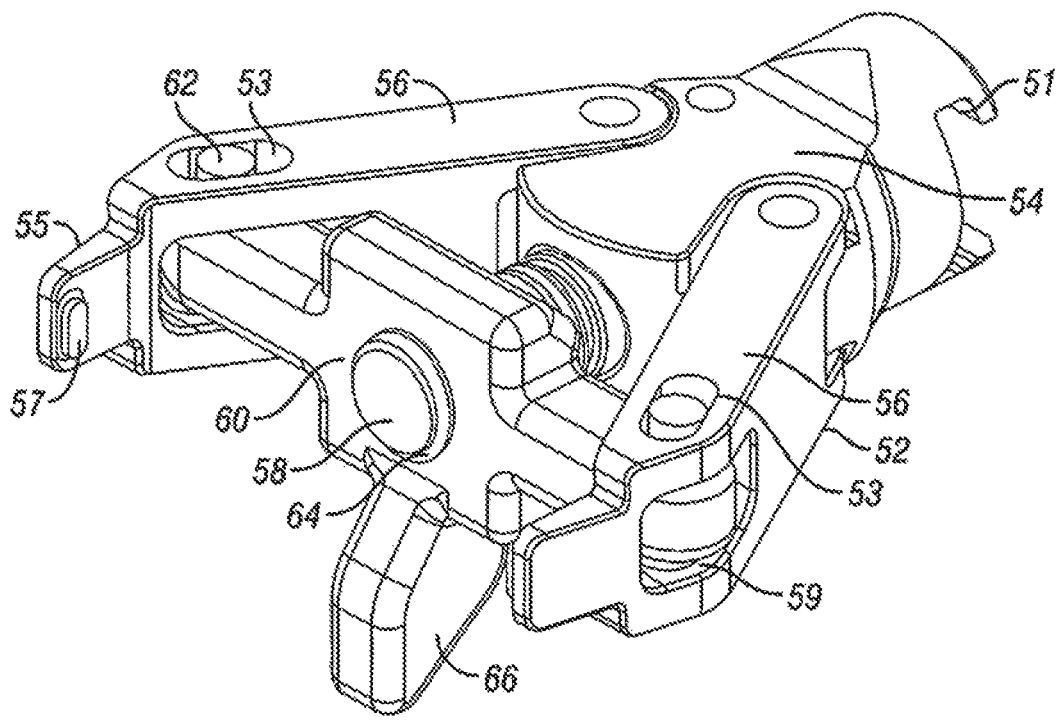
FIG. 8 is a perspective view of an example embodiment of a pronged attachment tip that can be used with the implant inserter of FIG. 1.
Figure 9:
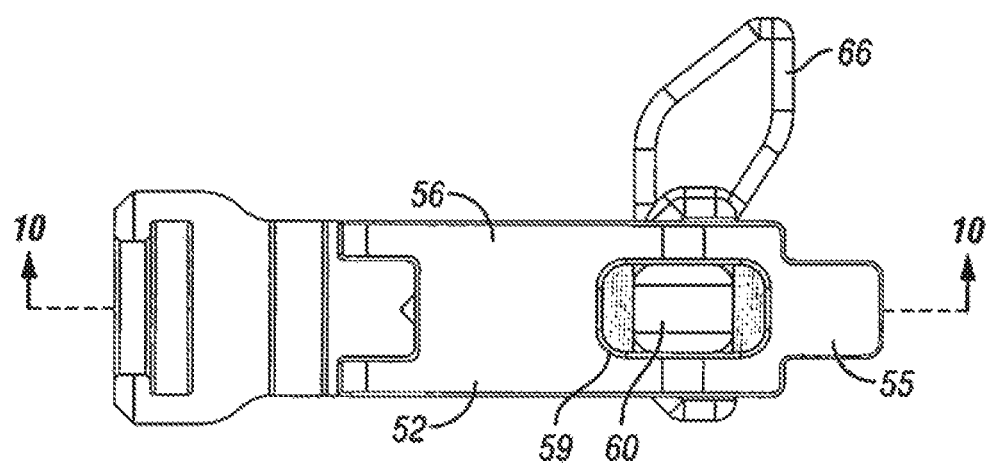
FIG. 9 is a side view of the attachment tip shown in FIG. 8.
Figure 10:
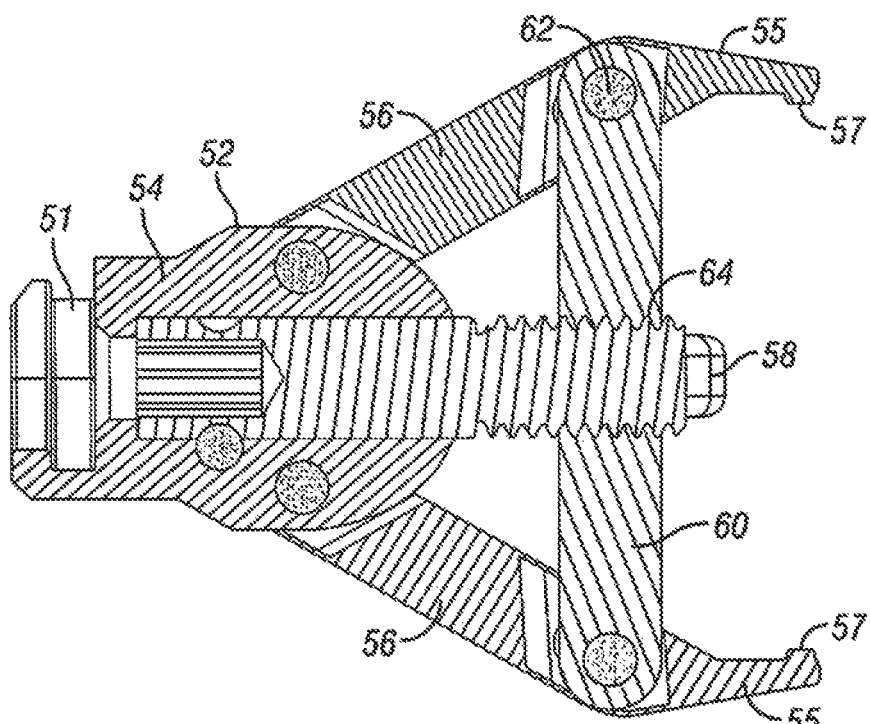
FIG. 10 is a top sectional view taken on line A-A of FIG. 9.

Referring to FIGS. 8-11, the pronged attachment tip 52 is adapted to grip an implant 6 and act as a retainer in a manner that is secure but can also easily be released when necessary. Referring to FIG. 9, implant 6 may include recesses 7 adapted to cooperate with ribs 57 to provide an interference fit between the pronged attachment tip 52 and implant 6. Prongs 56 are pivotable about base portion 54 to accommodate implants 6 of differing width, size and shape.

Referring to FIGS. 1, 3, 4, and 8, the attachment tip 40 and pronged attachment tip 52 are designed to be attached in multiple configurations relative to the general plane of operation of the inserter instrument 12. Referring to FIGS. 1 and 3, in an example embodiment, attachment tip 40 is oriented such that fin 50 projects upwardly (as shown) relative to the plane of the inserter instrument 12.

Referring to FIGS. 1 and 8, the pronged attachment tip 52 is oriented such that the fin 66 projects downwardly (as shown) relative to the plane of the inserter instrument 12. In another embodiment, the attachment tip 40 could be attached and configured so that the fin 50 projects orthogonally downwardly or upwardly, and the pronged attachment tip 52 could be configured so that the fin 66 projects orthogonally upwardly. In all of the foregoing configurations the fin would still slide along the tracking slots 38 to guide and ensure proper alignment of the attachment tip 40, 52. In an embodiment, the attachment tips may be made of steel composite. However, any material suitable for surgical applications may be used, such as but not limited to plastic, composite and metal.

Figure 11:
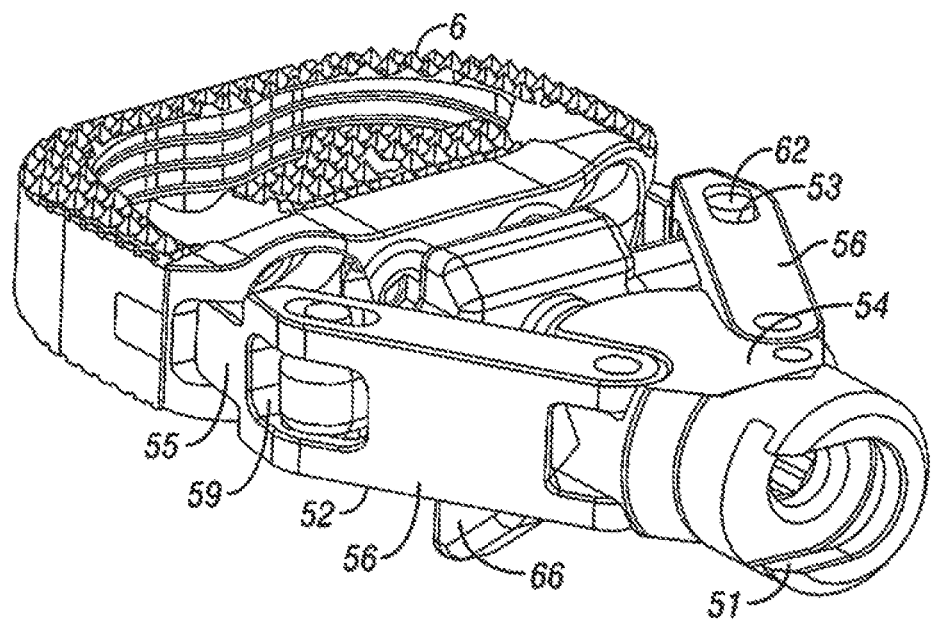
FIG. 11 is a perspective view of the attachment tip of FIG. 8 with an example embodiment of an implant.

Referring to FIGS. 1 and 11, in an example operation, implant inserter 10 is used during a surgical procedure to deliver an implant 6 to a disc space (not shown) formed between vertebrae. The inserter 12 is first set to a start position where the central shaft 16 is fully withdrawn and the tip of the central shaft 16 is proximate the distal end of the body. Next, a single distractor arm 38 or the pair of distractor arms 38 can be pivoted open to provide space to insert an attachment tip 40,52. For purposes of this example operation, the pronged attachment tip 52 is joined to the tip adapter 20 and central shaft 16.

The implant 6 can then be inserted into the pronged attachment tip 52 so that it is firmly gripped by the pronged attachment tip 52. Distractor arms 18 are pivoted to a closed position as shown in FIG. 1, such that the fin is aligned with and projects through either the upper or lower tracking slot 38 to ensure proper alignment and tracking. Next, the implant inserter 10 is placed so that the stop members 39 abut the outside of the vertebrae and the distal ends of the distractor arms 38 enter the disc space. Stop members 39 provide a stable support for the implant inserter 10 so that it does not become inadvertently dislodged during operation.

The central shaft 16 is driven forward by pushing or rotating the handle 11 depending on the mode of the actuator 23. As the central shaft 16 moves forward, the pronged attachment tip 52 and implant 6 move along in a distal direction towards the disc space. Also as the central shaft 16 moves forward, the distractor arms 38 move away from each other to effectively spread the disc space.

In an example embodiment, during the insertion process, the pronged attachment tip 52 and implant 6 are moved beyond the distal ends of the distractor arms 38. During the final insertion of the implant 6 into the disc space, the fin 66 can abut against the vertebrae. The tapered design of the fin tracks the profile of the vertebrae and provides additional support during final insertion of the implant 6 into the disc space, and for the start of withdrawal. After the implant 6 has been situated per requirements, the central shaft 16 may be pulled out of the surgical site by pulling freely, twisting the handle 11 or using the dial 13. This will move the central shaft 16 from a distal to proximal direction out of the space between the vertebrae.

In example embodiments, the implant inserter 10 can be used for posterior, lateral, oblique, anterior and other alternate approaches.

In the foregoing description and in the accompanying drawings, specific terminology and drawing symbols have been set forth to provide a thorough understanding of the disclosed embodiments. In some instances, the terminology and symbols may imply specific details that are not required to practice those embodiments.

Various modifications and changes may be made to the embodiments presented herein without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. An instrument for inserting an implant between adjacent vertebral bodies, comprising:
    a body having a bore;
    a central shaft, having a proximal end and a distal end, configured to rotationally move through the bore;
    a pair of distractor arms pivotally coupled to the body and configured to move apart during rotational movement of the central shaft to distract the adjacent vertebral bodies; and
    an attachment tip attached to the distal end of the central shaft to releasably connect the implant to the instrument, wherein the attachment tip comprises a screw thread tip to engage the implant and a pair of ribs configured to cooperate with recesses in the implant
    wherein the body includes a first tubular portion and a second tubular portion, the first tubular portion located centrally and the second tubular portion extending distally from the body, the second tubular portion is tapered and includes windows.

2. The instrument of claim 1, further comprising tracking slots formed in and extending through surfaces of and along a longitudinal axes of the distractor arms.

3. The instrument of claim 2, further comprising a guide member projecting outward from the attachment tip.

4. The instrument of claim 1, wherein the distal end of the central shaft has a tip adapter extending therefrom.

5. The instrument of claim 4, wherein the attachment tip is connectable to the tip adapter.

6. The instrument of claim 5, wherein the attachment tip includes a bore configured to receive the tip adapter.

7. The instrument of claim 1, further comprising a dial located at a proximal end of the central shaft.

8. The instrument of claim 7, wherein the dial is configured to rotate the screw thread tip to either engage or release the implant.

9. The instrument of claim 8, further comprising a handle connected to the central shaft.

10. The instrument of claim 9, wherein rotation of the handle causes rotation of the central shaft.

11. An instrument for inserting an implant between adjacent vertebral bodies, comprising;
a body having a bore;
a central shaft, having a proximal end and a distal end, configured to move through the bore;
a pair of distractor arms configured to move apart during rotational movement of the central shaft to distract the adjacent vertebral bodies;
an attachment tip attached to the distal end of the central shaft to releasably connect the implant to the instrument, wherein the attachment tip engages the implant, and wherein a pair of ribs on the attachment tip are configured to cooperate with recesses in the implant when the attachment tip engages the implant
wherein the body includes a first tubular portion and a second tubular portion, the first tubular portion located centrally and the second tubular portion extending distally from the body, the second tubular portion is tapered and includes windows.

12. The instrument of claim 11, further comprising tracking slots formed in and extending through surfaces of and along a longitudinal axes of the distractor arms.

13. The instrument of claim 12, further comprising a guide member projecting outward from the attachment tip.

14. The instrument of claim 11, wherein the distal end of the central shaft has a tip adapter extending therefrom.

15. The instrument of claim 14, wherein the attachment tip is connectable to the tip adapter.

16. The instrument of claim 15, wherein the attachment tip includes a bore configured to receive the tip adapter.

17. The instrument of claim 11, further comprising a dial located at a proximal end of the central shaft.

18. The instrument of claim 17, wherein the dial is configured to rotate the screw thread tip to either engage or release the implant.

19. The instrument of claim 18, further comprising a handle connected to the central shaft.

20. The instrument of claim 19, wherein rotation of the handle causes rotation of the central shaft.

* * * * *